United States Patent [19]
Hinsch et al.

[11] Patent Number: 6,162,962
[45] Date of Patent: Dec. 19, 2000

[54] AREAL IMPLANT

[75] Inventors: Bernhard Hinsch, Norderstedt; Christian Walther, Kattendorf, both of Germany

[73] Assignee: Ethicon GmbH & Co., KG, Germany

[21] Appl. No.: 08/823,914

[22] Filed: Mar. 25, 1997

[30] Foreign Application Priority Data

Mar. 26, 1996 [DE] Germany .......................... 196 13 730

[51] Int. Cl.$^7$ .............................. A61F 2/02; A61F 2/08; A61F 2/38; A61B 17/04
[52] U.S. Cl. ................................ 623/11; 623/13; 623/14; 623/15; 623/66; 606/151; 428/225
[58] Field of Search .................................. 623/11–15, 66; 606/151; 428/225

[56] References Cited

U.S. PATENT DOCUMENTS

| | | | |
|---|---|---|---|
| 4,655,221 | 4/1987 | Devereux | 128/334 R |
| 4,871,365 | 10/1989 | Dumican | 623/11 |
| 4,983,184 | 1/1991 | Steinemann | 623/66 |
| 5,185,195 | 2/1993 | Harpell et al. | 428/102 |
| 5,198,280 | 3/1993 | Harpell et al. | 428/102 |
| 5,569,273 | 10/1996 | Titone et al. | 623/11 |
| 5,658,343 | 8/1997 | Hauselmann et al. | 623/20 |

FOREIGN PATENT DOCUMENTS

| | | |
|---|---|---|
| 204 931 A1 | 4/1986 | European Pat. Off. |
| 38 30 005 C1 | 11/1989 | Germany . |
| WO 87/07495 | 12/1987 | WIPO .............. A61F 2/00 |
| WO 96/03 165 | 7/1995 | WIPO . |

*Primary Examiner*—Mickey Yu
*Assistant Examiner*—Choon P. Koh
*Attorney, Agent, or Firm*—Hal Brent Woodrow

[57] ABSTRACT

An areal implant, in particular for abdominal wall closure, has a flexible basic structure made from a knitted fabric comprising non-resorbable or slowly resorbable material or a combination of such materials. The knitted fabric of the basic structure is designed to stretch more than the tissue region destined to receive the implant below a critical force and stretch less than this tissue region above the critical force. The critical force lies below the highest load which is allowable for this tissue region. The basic structure is provided with a stiffening, synthetic resorbable material whose resorption time is less than that of the basic structure.

16 Claims, 8 Drawing Sheets

AREAL IMPLANT

FIELD OF THE INVENTION

The invention relates to an areal implant, in particular for abdominal wall closure.

BACKGROUND OF THE INVENTION

During an operation in the abdominal region, it is often necessary to strengthen the abdominal wall using an inserted areal implant. It is known to use nets made from the non-resorbable plastics polypropylene or polyester or from the slowly resorbable polyglactin 910 (a copolymer of glycolide and lactide in the ratio 9:1) for such implants. Metallic implants are also used.

The known implant nets have some disadvantages. For example, they are relatively heavy, i.e. the areal weight is as a rule more than 50 g/m$^2$ and predominantly even ca. 100 g/m$^2$. If the implants are not resorbable, a relatively large quantity of foreign substance thus remains permanently in the body. In terms of tearing strength, the known implant nets are frequently over-sized, i.e. they have a much higher strength than is required from a physiological viewpoint. These properties, combined with the usual, net-like construction of the basic structure of the previously known implants, can mean that the well-being and the mobility of a patient who is fitted with such an implant are limited.

Another disadvantage of the previously known areal implants is that, although they conform better to the abdominal wall after the operation if they are more flexible, they can then only be inserted with difficulty, since e.g. they fold readily. On the other hand, although a rigid implant is easy to handle, it can lead to problems in the long term after insertion into the abdominal wall, as already mentioned. The previously known areal implants are thus either too flexible for ease of working during an operation or too rigid for an unproblematical interaction with the abdominal wall into which they are inserted.

SUMMARY OF THE INVENTION

It is thus the object of the invention to provide an areal implant, in particular for abdominal wall closure, which can be worked easily during an operation and which shows an elasticity behavior in the long term which is matched to the tissue into which it is inserted.

This object is achieved by an areal implant, in particular for abdominal wall closure, having the features of claim 1. Advantageous embodiments result from the dependent claims.

DETAILED DESCRIPTION OF THE INVENTION

Figure 1A:
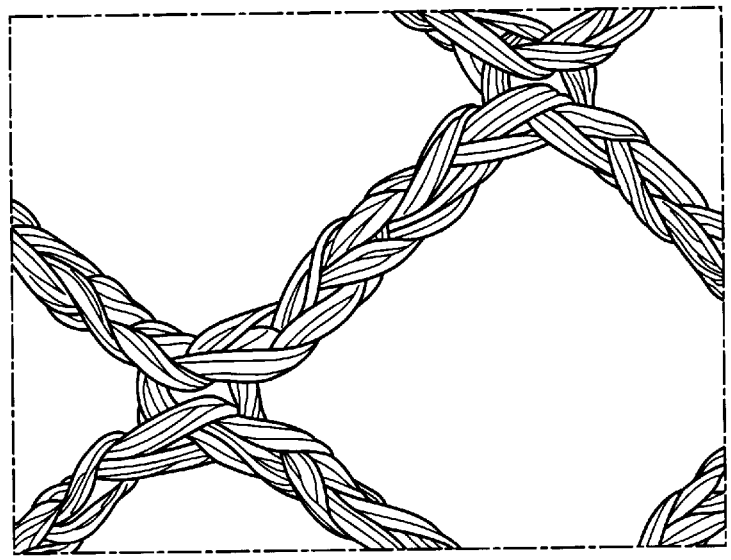
FIG. 1 is a magnified schematic view of a first version of the flexible basic structure (variant A), magnified 25 times in part (a) and 15 times in part (b)

The areal implant according to the invention has a flexible basic structure made from a knitted fabric comprising non-resorbable material or resorbable material or a combination of such materials. If resorbable material is used, the resorption time (i.e. the period after which the total mass of the implant has degraded in vivo) is at least 60 days, and/or the in vivo decrease in strength is so slow that 30 days after implantation the tearing strength is still at least 10% of the initial tearing strength. Non-resorbable or slowly resorbable materials are used in order that the basic structure is stable in the longer term and a more certain healing success can be ensured.

The term "knitted fabric" is to be understood here in the widest sense. It also includes, for example, knits and other mesh structures, i.e. essentially all textile materials which are not pure woven fabrics.

The knitted fabric of the basic structure is designed to stretch more than the tissue region destined to receive the implant below a critical force and stretch less than this tissue region above the critical force. The critical force is below the highest load this tissue region can be submitted to. The flexible,basic structure is thereby matched without problems to the usual movements of the tissue (e.g. of an abdominal wall) into which the areal implant is inserted or sewn. In the case of small forces, as occur during normal movements by the patient, the elasticity behavior of the system consisting of an abdominal wall and the inserted implant is shaped by the abdominal wall. The implant thus does not act as a foreign body. If, on the other hand, the forces exceed the critical force, the implant absorbs the forces and thus prevents injury to the body tissue, e.g. the abdominal wall.

According to the invention, the basic structure is stiffened by a synthetic resorbable material whose resorption time is less than that of the basic structure and preferably lies in the range from 2 days to 200 days. As a result, the areal implant is relatively firm and easy to handle during the operation (e.g. when cutting to size and inserting) but loses its then undesired rigidity after a relatively short time in the body tissue, because the stiffening synthetic material is resorbed.

In a preferred version, the knitted fabric of the basic structure is constructed in such a way that it has stress/strain properties which can be quantified using a plunger pressing test, as stated in claim 2.

The areal weight of the basic structure is preferably less than 50 g/m². When suitable materials are used (see below), for an implant for abdominal wall closure of correspondingly low mass, a strength can be achieved which lies above the physiological framework data given by Klinge (U. Klinge, B. Klosterhalten, W. Limberg, A. P. Ottinger, V. Schumpelick: Use of mesh materials in scar rupture; Change in the abdominal wall dynamics after mesh implantation; Poster, 162nd Convention of the Lower RhineWestphalian Surgeon's Association, 1995). According to him, the intra-abdominal pressure is 20 kPa (150 mm Hg) at most, the wall stress at the edge of an abdominal tissue region 16 N/cm at most and the tearing strength of the fasciae, 20 N/cm to 30 N/cm. An implant constructed in this way is thus able to absorb all forces occurring physiologically at a healthy abdominal wall and also offers an additional safety reserve. More stable and thus heavier basic structures offer no additional advantage, but can have the disadvantage of undesired rigidity mentioned at the beginning.

The knitted fabric of the basic structure preferably has an approximate rectangular structure or approximate quadratic structure knitted from yarns. Honeycomb structures or structures with approximately circular openings or other polygonal structures are however also conceivable. Preferred versions of such knitted fabrics are explained in more detail in the description of the embodiments with the help of Figures. The desired stress/strain behavior can be achieved with knitted structures of this type, i.e. the basic structure stretches more than the tissue region destined to receive the implant below the critical force and less than this tissue region above the critical force, the critical force being below the highest load allowable for this tissue region.

There are various possibilities for connecting the stiffening material to the basic structure. Thus, the stiffening material can e.g. have resorbable yarns or thin monofilaments woven into the basic structure, it can have a film which is applied to one side or both sides of the basic structure, or it can have a coating applied to the material of the knitted fabric. Combinations of these are also conceivable.

Suitable materials for the basic structure include but are not limited to polyamides (e.g. nylon-6, nylon 6,6, nylon 610, etc.) polyolefins (e.g. polyethylene, polypropylene [including isotatic and syndiotactic polymers] and copolymers of polyethylene and polypropylene), polyesters (e.g. polybutylene terephthalate, polyethylene terephthalate, etc.) hydrolyzable aliphatic polyesters (e.g. polymers containing glycolic acid repeating units, lactic acid repeating units, (including l, d, dl and meso lactide and combinations thereof), 3-methyl-1,4-dioxan 2,5-dione, 3,3-diethyl-1,4-dioxan-2,5-one, 1,4-dioxan-2-one, 1,4-dioxepan-2-one, 1,5-dioxepan-2-one, delta-valerolactone, epsilon-decalactone, pivalolactone, gamma-butyrolactone, ethylene carbonate, 1,3-dioxan-2-one, 4,4-dimethyl-1, 3-dioxan-2-one, epsilon-caprolactone, combinations and blends thereof.)

Preferred materials are yarns of polypropylene, polyethylene and polyglactin 910 (a copolymer composed of about 90 percent by weight glycolide and about 10 percent by weight lactide) polylactide, polyglycolide, mixture and combinations of such yarns.

Suitable stiffening materials are hydrolyzable materials including but not limited to yarns or films of hydrolyzable aliphatic polyesters (e.g. polymers containing glycolic acid, lactic acid, glycolide, lactide (l, d, dl and meso lactide and combinations thereof), 3-methyl-1,4-dioxan-2,5-dione, 3,3-diethyl-1,4-dioxan-2,5-one, 1,4 dioxan-2-one, 1,4-dioxepan-2-one, 1,5-dioxepan-2-one, delta-valerolactone, epsilon-decalactone, pivalolactone, gamma-butyrolactone, ethylene carbonate, 1,3-dioxan-2-one, 4,4-dimethyl-1, 3-dioxan-2-one, epsilon-caprolactone, combinations and blends thereof).

Advantageous materials for the basic structure are e.g. polypropylene, polyester, polyglactin 910, polylactide yarns, polyglycolide yarns, poly-p-dioxanone yarns, but also copolymers, mixtures or combinations of such materials.

Suitable as the stiffening material are e.g. yarns or films of poly-p-dioxanone, yarns or films of polyglactin (i.e. glycolide/lactide copolymers), yarns or films of polylactide, yarns or films of other copolymers of these materials, monofilaments of such materials (e.g. with thread thicknesses of 0.01 mm to 0.2 mm in diameter), coating waxes made from such materials, in particular from polyglactin 630 and others. Mixtures of synthetic resorbable materials whose resorption time lies in the desired range can also be used for the stiffening material. If the stiffening material is of a textile nature, the result of the in vivo decrease in strength is that, after an implantation time of typically 2 to 50 days, the residual tearing strength is still about 10% of the initial tearing strength.

The material of the basic structure is preferably not dyed, in order that the basic structure, which does after all remain in the body for a long time or permanently after implantation, shows no undesired foreign body reaction as a result of the dye. On the other hand, it can be advantageous if the stiffening material is dyed. This does in fact permit a better visual check on the implant during the operation. During resorption the dye disappears, so that no dye remains in the body in the longer term and thus no undesired side-effects occur.

FIGS. 1 to 5 show magnified schematic views of different versions of the knitted fabric of the flexible basic structure of the areal implant according to the invention. The figures are drawn on the basis of scanning electron microscope photographs taken at roughly 25 times magnification.

Figure 1B:
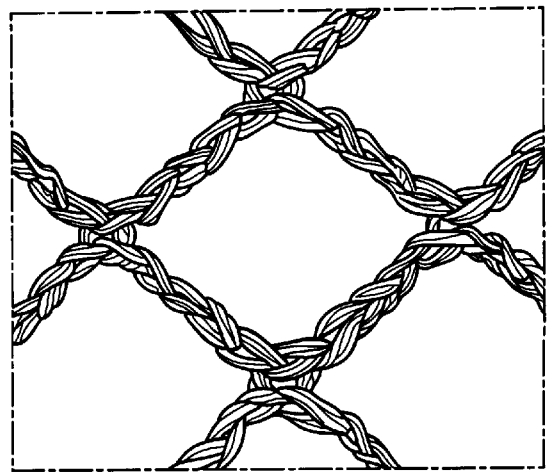
Figure 2:
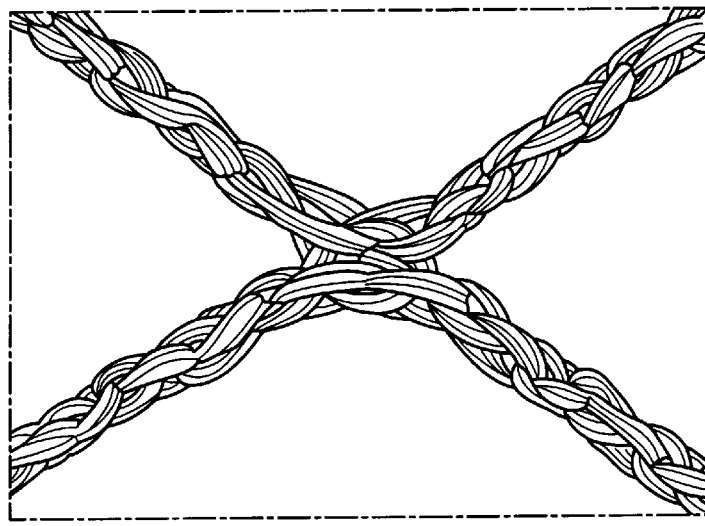
FIG. 2 is a magnified (25 times) schematic view of another version of the flexible basic structure (variant B)
Figure 3:
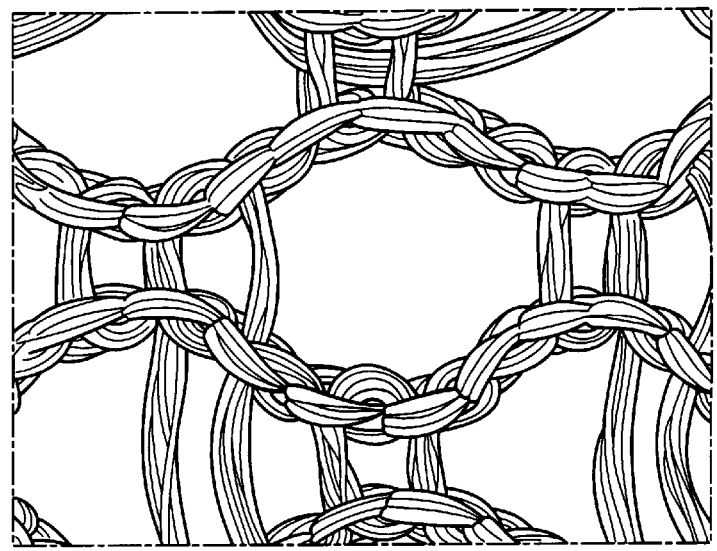
FIG. 3 is a magnified (25 times) schematic view of another version of the flexible basic structure (variant C)
Figure 4:
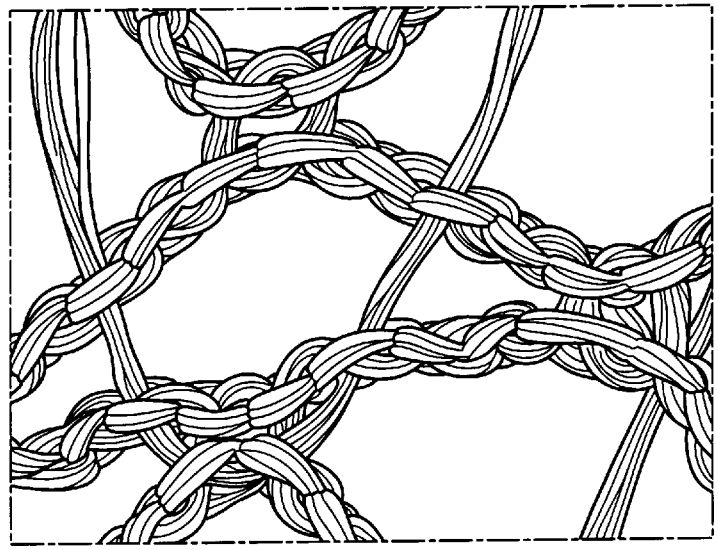
FIG. 4 is a magnified (25 times) schematic view of another aversion of the flexible basic structure (variant D)
Figure 5:
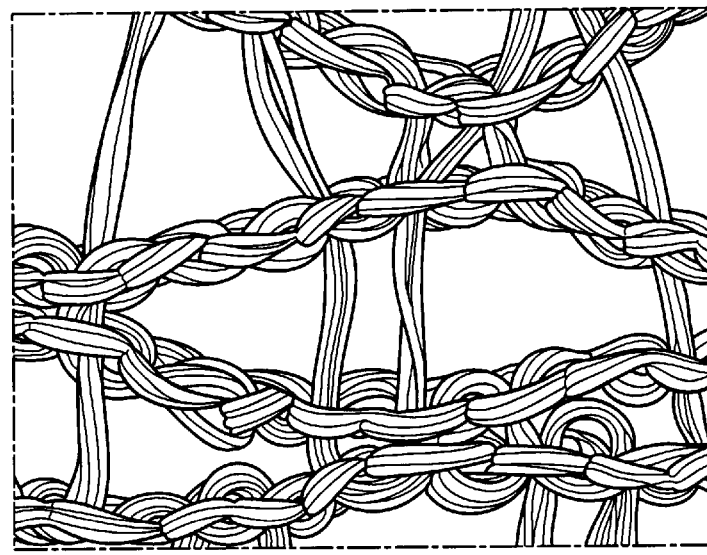
FIG. 5 is a magnified (25 times) schematic view of another version of the flexible basic structure (variant E)

Variant A of the knitted fabric according to FIG. 1 has an approximate quadratic structure, the crosspiece length-being about 3 mm in each case. Variant B of the knitted fabric according to FIG. 2 also has an approximate quadratic structure. However, the crosspiece length is larger here and is about 5 mm. Variant C of the knitted fabric, shown in FIG. 3, has differently sized openings or pores, the area of the large pores being greater than 0.5 mm² and that of the smaller pores being less than 0.5 mm². Variants D and E of the knitted fabric, shown in FIGS. 4 and 5, have other structures.

It is clearly recognizable from FIGS. 1 to 5 that the majority of the pores are larger than 0.5 mm². Thus, after implantation, the flexible basic structure of the areal implant can be grown through by tissue in satisfactory manner, which leads to a secure anchorage in the body of the patient and to a reliable absorption of forces by the implant.

TABLE 1

Data for five flexible basic structures according to the invention (variants A to E) and for a conventional implant net (H) made of polypropylene (polypr.)

| | Variants | | | | | |
|---|---|---|---|---|---|---|
| | A | B | C | D | E | H |
| Material | Polypr. | Polypr. | Polypr. | Polypr. | Polypr. | Polypr. |
| Filament | multifilament | multifilament | multifilament | multifilament | multifilament | monofilament |
| Thread systems | 3 | 3 | 3 | 3 | 3 | 1 |
| Number of courses per cm (longitudinal) | 220 | 220 | 160 | 186 | 212 | 62 |
| Number of wales per cm (transverse) | 52 | 38 | 57 | 64 | 72 | 46 |
| Yarn fineness in tex [g/1000 m] | 6.7 | 6.7 | 6.7 | 6.7 | 6.7 | 20.6 |
| Pore size (approx.) of the pores > 0.5 mm$^2$ [mm$^2$] | 3 × 3 | 4 × 4 | 1.3 × 1.3 | 2 × 3.3 | 1.3 × 3.3 | |
| Proportion of pores [%] | 93 | 95 | | | | 83.5 |
| Thickness [mm] | 0.41 | 0.4 | | | | 0.7 |
| Areal weight [g/m$^2$] | 26.8 | 20.1 | 31.4 | 36.2 | 40 | 109 |
| Seam tear-out force per cm (longitudinal) [N/cm] | 17.5 | 13.5 | 20.1 | 20.7 | 23 | 57 |
| Seam tear-out force per cm (transverse) [N/cm] | 22.7 | 22.4 | 26.3 | 31.7 | 36.1 | 75 |
| Plunger pressing test (similar to DIN 54307) | | | | | | |
| $F_{max}$ [N] | 464 | 415 | 460 | 488 | 625 | 2370 |
| Plunger path length at $F_{max}$ [mm] | 44.5 | 44.1 | 40.4 | 40.6 | 44.8 | 44.7 |
| Stress at $r_{contact}$ [N/cm] | 17.7 | 16.1 | 18.8 | 19.9 | 23.8 | 90.9 |
| Deformation [%] | 34.5 | 33.9 | 28.6 | 28.9 | 34.9 | 34.1 |
| Elongation at break [%] | 39.5 | 39.1 | 35.8 | 36.0 | 39.7 | 39.7 |
| Strip tensile test | | | | | | |
| Tearing strength (longitudinal) [N/cm] | 33 | 25 | 33 | 37 | 45 | 150 |
| Elongation at break (longitudinal) [%] | 37.9 | 28.2 | 25.2 | 49.5 | 40.3 | 80.4 |

Given in Table 1 are data for the individual variants A to E of the flexible basic structure of the areal implant according to the invention and, for comparison, the corresponding data for a conventional implant net. All the fabric was knitted on a Crochet Galoon knitting machine.

Variants A to E are all knitted from multifilament polypropylene, using three thread systems. The conventional implant net consists of monofilament polypropylene, using one thread system. Table 1 shows the number of courses per centimeter, the number of wales per centimeter, the yarn fineness, the dimensions of the pores larger than 0.5 mm$^2$, the proportion of pores (relative to the total area of the knitted fabric or of the conventional implant net) and the thickness. Compared with the conventional implant net, variants A and B have a larger proportion of pores and a smaller thickness. As Table 1 also shows, variants A to E have a relatively low areal weight, which in all cases is below 50 g/m$^2$ and is thus clearly smaller than that of the conventional implant net.

For variants A to E, the seam tear-out force per centimeter of seam length, measured along and across the knitted fabric or the conventional implant net, is as a rule more than 16 N/cm, the value quoted by Klinge for the maximum wall stress at the edge of an abdominal tissue region.

The stress-strain behavior of the knitted fabrics or of the conventional implant net can be best described quantitatively using a plunger pressing test related to DIN 54307. In the textile industry, material properties related to area are measured with such plunger pressing tests.

Figure 6:
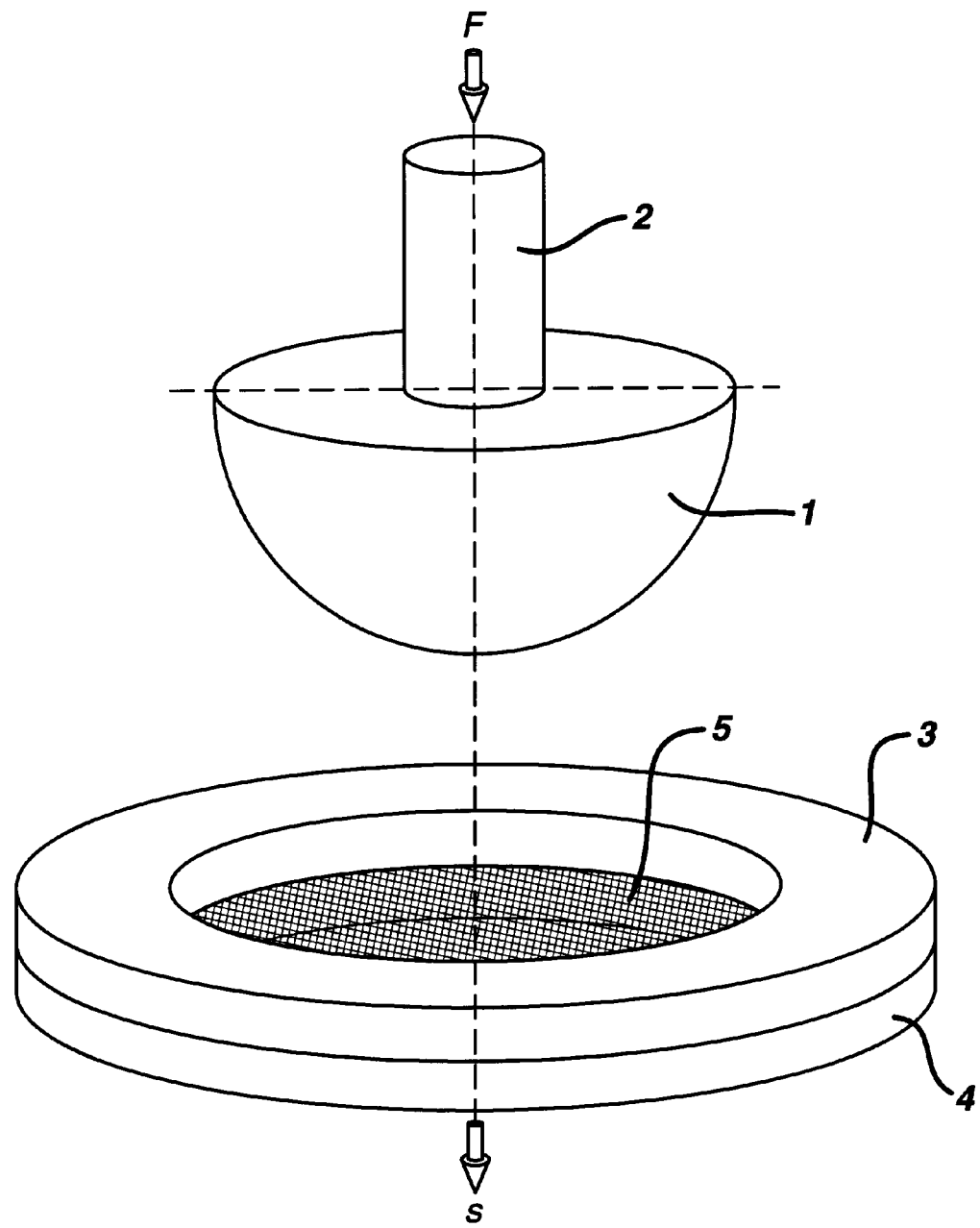
FIG. 6 is a schematic view 3 of a device for carrying out plunger pressing tests.

FIG. 6 shows a schematic view of a device for carrying out plunger pressing tests. A semispherical plunger 1, which is attached to a shank 2, is moved in the direction of the arrow, i.e. along the axis of symmetry. A sample 5 of the knitted fabric to be investigated or of a conventional implant net is clamped between an upper ring 3 and a lower ring 4.

When the plunger 1 is advanced in a downwards direction, it pushes the sample 5 in a downwards direction. The greater the deformation of the sample 5, the greater the force F exerted on the plunger 1 by the sample 5 becomes. The force F and the plunger path length s, which is a measure of the deformation of the sample 5, are measured, wherein s=0 when the lowest point of the plunger 1 is located in the plane of the sample 5. With the device used for the plunger pressing tests the plunger radius is 50 mm. The internal radius of the upper ring 3 and of the lower ring 4 is 56.4 mm, so that the effective surface area of the sample 5 is 100 cm$^2$.

Given in Table 1 for variants A to E and for the conventional implant net are the maximum force $F_{max}$ applied during the plunger pressing test, at which the first damage to the sample occurs (in the middle region of the sample), and the associated plunger path length $s_{max}$. From this, the so-called stress at $r_{contact}$, which corresponds to the so-called wall stress in N/cm, can be calculated. In the sample, the stress at $r_{contact}$ occurs along the circular line where, in the case of plunger path length $s_{max}$, the sample region abutting the plunger passes into the sample edge region which does not touch the plunger directly and extends as far as the rings 3, 4. At this stress, the deformation given in Table 1 arises which results from the change in length of the sample at $r_{contact}$ measured in the peripheral direction, relative to the corresponding peripheral length of the non-deformed sample. From the test data, it is also possible to calculate the elongation at break, also given in Table 1, which is higher than the deformation since the sample in the plunger pressing test tears, not at $r_{contact}$, but in the middle region where it is more stretched than at $r_{contact}$.

It is clear from Table 1 that for all variants A to E the stress at $r_{contact}$ is greater than or equal to 16 N/cm, i.e. at least as large as the maximum wall stress at the edge of an abdominal tissue region (16 N/cm) quoted by Klinge. The much greater value in the case of the conventional implant net is physiologically unnecessary.

Table 1 also shows the results of a strip tensile test carried out on samples of variants A to E and the conventional implant net. For this, the tearing force per centimeter of sample width (tearing strength) along the sample direction and the elongation at break are determined. It is, however, to be taken into consideration here that the values can be severely distorted by the test (contraction upon drawing), making the plunger pressing test more informative.

For variants A to E of the knitted fabric, the tearing strengths lie in the range from 25 to 45 N/cm and are therefore at least as large as the tearing strength of the fasciae quoted by Klinge (20 to 30 N/cm). The much higher tearing strength of the conventional implant net is again not necessary.

Figure 7:
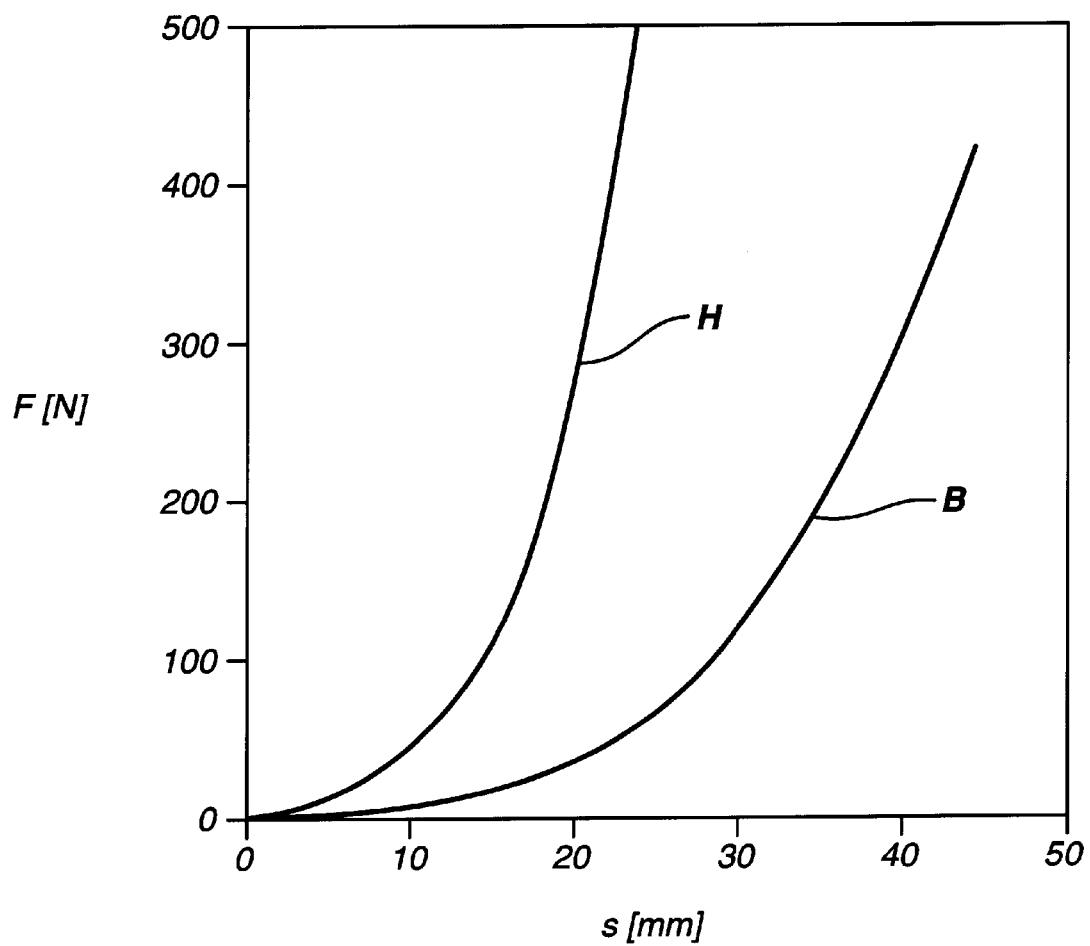
FIG. 7 is the plunger force—plunger path length diagram, measured with the device acording to FIG. 6, of the flexible basic structure according to variant B compared with a conventional implant made of polylpropylene (H)

FIG. 7 shows a complete plunger force—plunger path length diagram, determined using a plunger pressing test, for the knitted fabric of variant B compared with the conventional implant net made of polypropylene (H). The curve for variant B ends at the values for $F_{max}$ and $S_{max}$ given in Table 1, whilst the curve for the conventional implant net is not shown in full, but stops at F=500 N. It is clear to see that, for the implant of the invention according to variant B, the plunger force F is small even with relatively large plunger path lengths s. Only at larger values of s does the curve rise sharply. With the conventional implant net, the plunger force F is already large at average plunger path lengths s.

The plunger force—plunger path length diagrams as in FIG. 7 can be converted into force-length change diagrams or into stress-strain diagrams. In the case of the latter, stress is to be understood as the force per centimeter of sample width.

Figure 8:
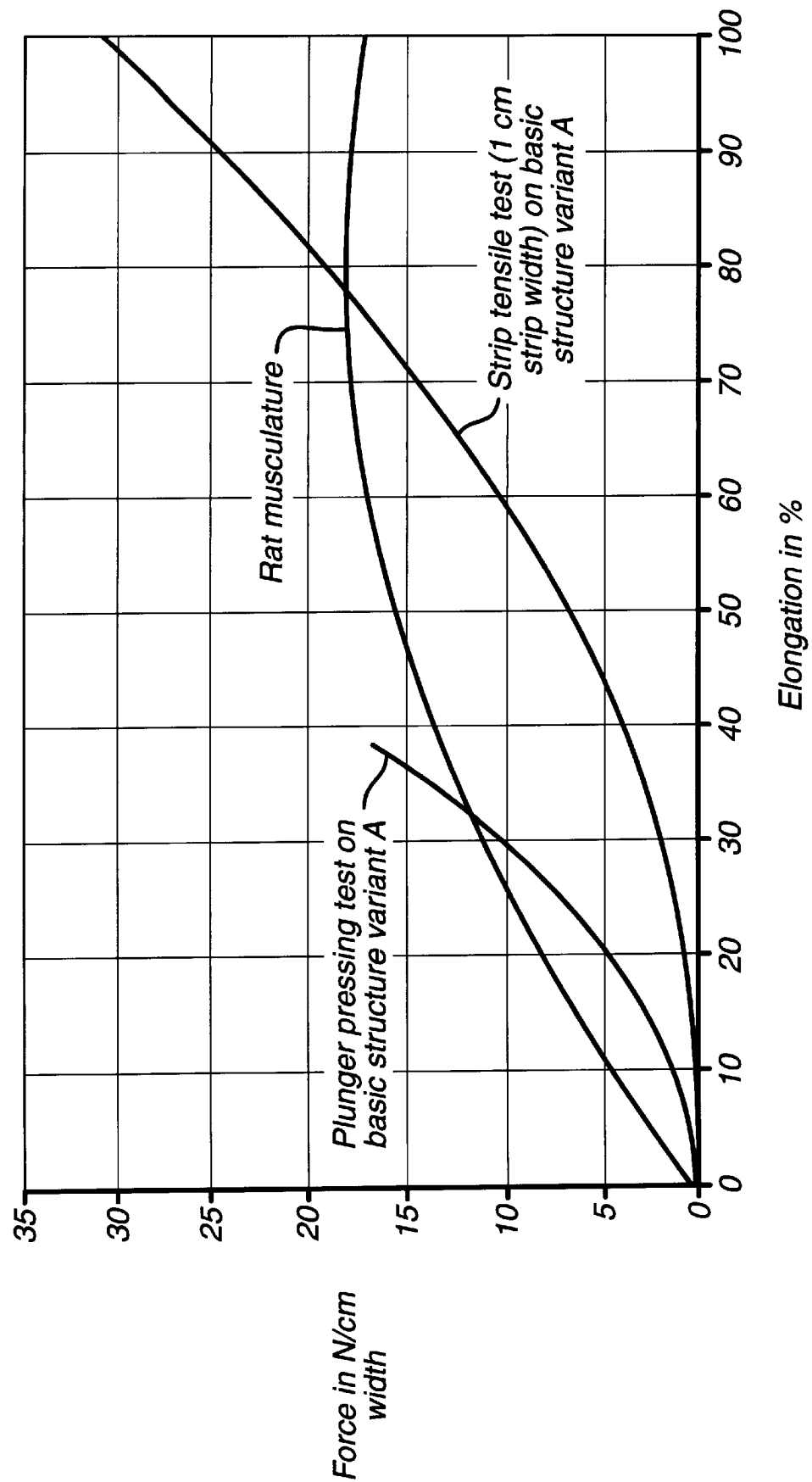
FIG. 8 is the stress-strain diagram of the flexible basic structure accorading to variant A, compared with rat musculature.

Moreover, the change in length of the sample is related to the total length of the sample (before strain) and is thus independent of the total length of the sample itself. FIG. 8 shows such a stress—strain diagram of the flexible basic structure according to variant A, as results from the plunger pressing test.

A stress—strain diagram determined using rat musculature is also shown, which was not, however, obtained by a plunger pressing test, which was not possible to carry out with rat musculature because of the sample size required, but on the basis of a strip tensile test on a sample strip approximately 1 cm in width. Measurements on the rat musculature were taken at a musculature thickness which corresponds approximately to that of a human abdominal wall, wherein the spread, as in the case of any biological sample, can be correspondingly large.

A narrow sample strip contracts in the tensile test, which leads to a much greater elongation at a given tensile force per strip width (stress) than if elongation takes place simultaneously in several spatial directions, as during the plunger pressing test. The curve for the rat musculature cannot, therefore, be compared directly with the stress—strain diagram obtained in the plunger pressing test for the flexible basic structure according to variant A. For this reason, another stress-strain diagram is shown for the flexible basic structure according to variant A which, as with the rat musculature, was determined using a strip tensile test, using a sample strip 1 cm in width. Even at an elongation of 100%, the sample had still not torn, which is not inconsistent with the elongation at break given in Table 1 for the strip tensile test, because the values in Table 1 apply to strips with a larger width.

In order to achieve an elongation up to about 78%, the forces required for variant A are smaller than for rat musculature, and for elongations of less than 50%, even much smaller. This means that a knitted fabric according to variant A implanted into muscle stretches with it during usual movements, without appreciable forces being necessary for this. Therefore, the implant does not have an inconvenient effect. However, if in the case of extreme loads, the forces which arise approach the highest load which is allowable for the tissue region into which the implant is inserted (which corresponds in FIG. 8 to about 18 N/cm), the knitted fabric of the basic structure undergoes less pronounced further stretching than the tissue, so that the knitted fabric of the basic structure is able to absorb the forces. The transition between the two elongation or stretching regions takes place at a critical force which results from the point of intersection of the curves in FIG. 8. The critical force defined in this way should be below the highest load which is allowable for the tissue region.

The fact that in FIG. 8 the critical force and the highest load which is allowable for the tissue region (to be more precise, the corresponding stresses) are approximately the same size is due to the tests with rat musculature which are difficult to carry out. FIG. 8 is intended only to illustrate the two described elongation regions. Quantitative measurements on the flexible basic structures are better carried out using plunger pressing tests, and Klinge's data can for example be referred to for tissue, see above.

Table 2 shows the plunger forces F measured in the plunger pressing test as a function of the plunger path length s for variants A to E, i.e. values as are shown graphically in FIG. 7 for variant B. By way of comparison, the values for the conventional implant net made of polypropylene (H) according to Table 1 and for another conventional implant net made of polyester (M) are also listed. The data for $F_{max}$ and for the plunger path length at $F_{max}$ are taken from Table 1. In the plunger pressing test initial damage to the investigated sample takes place at $F_{max}$.

Table 2 Plunger force F measured in the plunger pressing test related to DIN 54307 as a function of the plunger path length s, and $F_{max}$ (in N) and s ($F_{max}$) (in mm) for five flexible basic structures according to the invention (variants A to E) and for two conventional implant nets made of polypropylene (H) and of polyester (M).

| s [mm] | A F[N] | B F[N] | C F[N] | D F[N] | E F[N] | M F[N] | H F[N] |
|---|---|---|---|---|---|---|---|
| 10 | <10 | <10 | <10 | <10 | <10 | ca.10 | ca.50 |
| 15 | ca.-15 | ca.20 | ca.10 | ca.20 | ca.10 | ca.35 | ca.135 |
| 20 | ca.-30 | ca.35 | ca.30 | ca.40 | ca.40 | ca.85 | ca.300 |
| 25 | ca.-70 | ca.70 | ca.75 | ca.80 | ca.80 | ca.160 | ca.600 |
| 30 | ca.-130 | ca.130 | ca.150 | ca.170 | ca.150 | ca.280 | |
| $F_{max}$ | 464 | 420 | 460 | 490 | 630 | 460 | 2370 |
| s ($F_{MAX}$) | 45 | 44 | 40 | 41 | 45 | 37 | 45 |

As already seen, $F_{max}$ is much larger for the conventional implant net made of polypropylene than for variants A to E. $F_{max}$ for the conventional implant net made of polyester is of the same order of magnitude as for variants A to E. However, for the plunger path lengths up to 30 mm listed in Table 2, the plunger force for variants A to E is much smaller than for the conventional implant net made of polyester, which again illustrates the superiority of the implant according to the invention.

Figure 9:
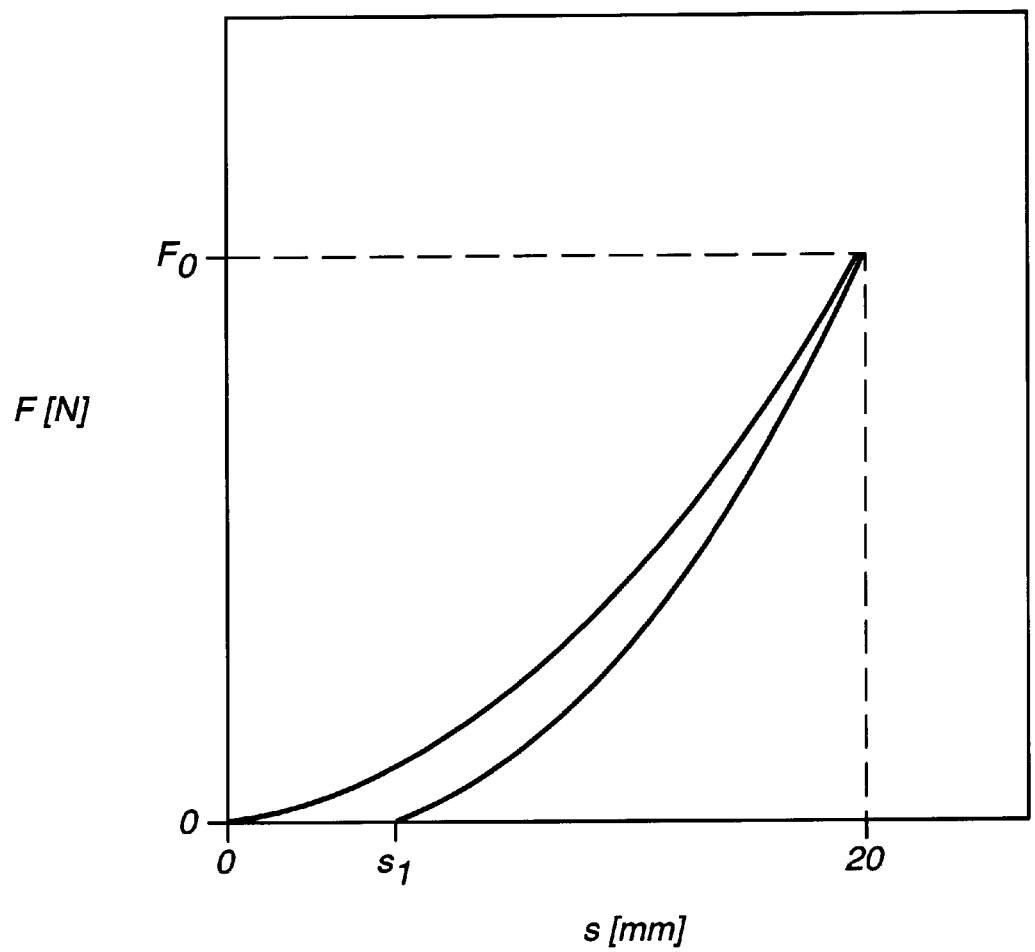
FIG. 9 is a schematic plunger force-plunger path length diagram to explain the hysteresis behavior of the flexible basic structure.

Both the knitted fabric of the basic structure of the areal implant according to the invention and conventional implant nets show a hysteresis behavior which can be determined in the plunger pressing test. The plunger force—plunger path length diagram in FIG. 9 shows schematically how in the case of a new sample the plunger force F, starting from the plunger path length s=0, increases to a value Fo which is defined here as the value of the plunger force at a plunger path length of 20 mm. If the plunger is withdrawn, the plunger force already returns to zero at a plunger path length $s_1$.

Table 3 compares the force $F_o$ and the plunger path length $s_1$, during one plunger pressing test (n=1) and after 5,000 plunger pressing tests (n=5,000) for a conventional implant net made of polyglactin 910, a conventional implant net made of polypropylene and the knitted fabric of the basic structure according to variant B. In order to ensure a secure abutment of the sample against the plunger, the force was not returned to zero in the plunger pressing tests (as in FIG. 9), but operated at a residual force of 0.5 N. It is clear from Table 3 that variant B of the flexible basic structure of the implant according to the invention offers a clearly lower resistance to the alternating load, which is to simulate the movement of an abdominal wall, than do the conventional implant nets.

Table 3 Hysteresis behavior of different implants after n alternating loads, measured in the plunger pressing test at a plunger path length between 0 and 20 mm and a plunger residual force of 0.5 N; see text

| Implant | n = 1 | | n = 5000 | |
|---|---|---|---|---|
| | $F_o$ [N] | $S_1$ [MM] | $F_o$ [N] | $S_1$ [MM] |
| Conventional implant net made of polyglactin 910, coarse-meshed | ca.150 | ca.8 | ca.114 | ca.15.5 |
| Conventional implant net made of polypropylene | ca.240 | ca.4 | ca.164 | ca.12.5 |
| Basic structure according to the invention, variant B | ca.45 | ca.7.5 | ca.30 | ca.14.2 |

Figure 10:
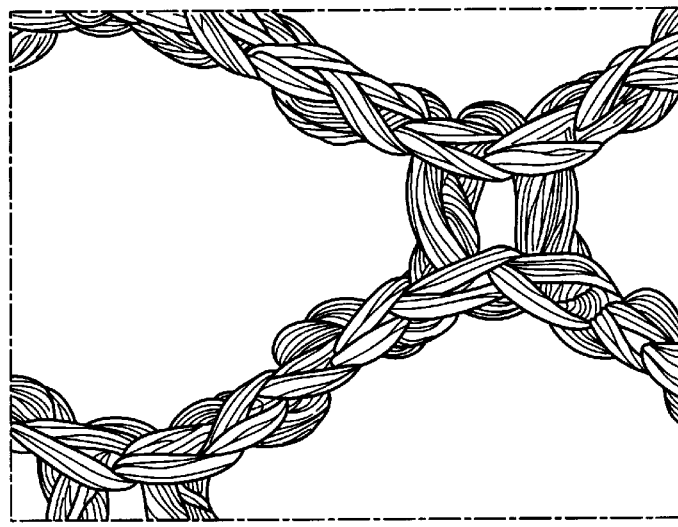
FIG. 10 is a magnified (25 times) schematic view of the flexible basic structure according to variant A which is stiffened with a yarn made of polyglactin 910.
Figure 11:
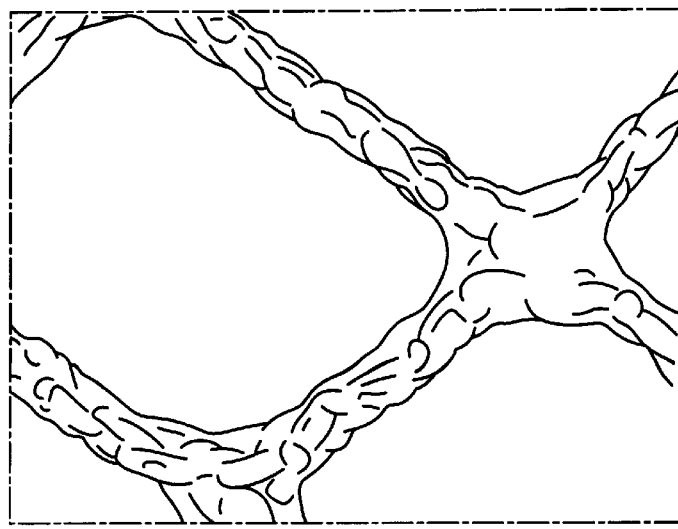
FIG. 11 is a magnified (25 times) schematic view of the flexible basic structure according to variant B which is stiffened with a resorbable coatng made of polyglactin 630 (a copolymer of glycolide and lactide in the ratio of about 6:3).

FIG. 10 shows a magnified schematic view of the flexible basic structure according to variant A, into which a multifilament thread made of polyglactin 910 is woven for stiffening. Shown in FIG. 11 is a magnified schematic view of the flexible basic structure according to variant B which is provided with a coating of polyglactin 630. Polyglactin 630 is a copolymer of glycolide and lactide in the ratio 6:3 and, just like polyglactin 910, is resorbable.

The flexible basic structure is stiffened by the woven-in thread or by the coating, as a result of which handling of the implant according to the invention during use, in particular during the operation, is much improved. Since the stiffening material is resorbable, the rigidity of the implant in the body of the patient decreases with time, until the implant has achieved the properties of the basic structure with its favorable stress/strain behavior, as explained earlier. Table 4 compares the bending resistances of the knitted fabric according to variant A (FIG. 1), of the knitted fabric according to variant B (FIG. 2), of the knitted fabric according to variant A with stiffening thread (FIG. 10), of the knitted fabric according to variant B with stiffening coating (FIG. 11) and of a conventional implant net made of polypropylene. The bending resistances quoted were determined in a three-point bending test with the supports 15 mm apart and a sample width of 15 mm. The conventional implant, rated as good by users as regards handling, has a bending resistance of ca. 0.15 to 0.20 N/mm. The bending resistances of the stiffened knitted fabrics are clearly higher than those of the original basic structures and are between ca. 0.05 and 0.42 N/mm. The latter value is even much higher than that for the previously known implant net.

TABLE 4

Bending resistance of different implants, determined by comparative measurement in the three-point bending test with the supports 15 mm apart and a sample width of 15 mm

| Implant | Bending resistance [N/mm] |
|---|---|
| Basic structure according to the invention, variant A | ca.0.03 |
| Basic structure according to the invention, variant B | ca.0.015 |
| Basic structure according to the invention, variant A, stiffened by yarn (4 × 80 den) made of polyglactin 910 | ca.0.05 |
| Basic structure according to the invention, variant B, stiffened by coating made of polyglactin 630 | ca.0.42 |
| Conventional implant net made of polypropylene | ca.0.15 to 0.2 |

The initial rigidity of the areal implant according to the invention can be varied within wide limits by means of the type, the quantity and the structure of the applied or incorporated stiffening resorbable material.

We claim:

1. An areal implant comprising:
    a flexible knitted fabric having an initial tearing strength which optionally has a resorption time of at least 60 days,
    wherein the flexible knitted fabric is designed to stretch more than a tissue region destined to receive the implant below a critical force and stretch less than the tissue region above the critical force, the critical force being below a highest load allowable for this tissue region, and
    a synthetic resorbable material, which stiffens the flexible knitted fabric, whose resorption time is less than that of the flexible knitted fabric, wherein the synthetic resorbable material is selected from the group consisting of yarns, monoflaments, and combinations thereof.

2. The areal implant according to claim 1, wherein the flexible knitted fabric is constructed in such a way that a plunger pressing test carried out on an implant 100 cm² in area with semispherical plunger 50 mm in radius produces a plunger force-plunger path length diagram which corresponds to a force-length change diagram, in which the plunger force is at most 15 N up to 10 mm plunger path length, less than 50 N at 20 mm plunger path length, and less than 200 N at 30 mm plunger path length, and in which the plunger force for plunger path lengths of more than 30 mm increases sharply to a value between 200 N and 1000 N at a plunger path length of 38 mm.

3. The areal implant of claim 1 characterized in that the resorption time of the synthetic resorbable material is 2 days to 200 days.

4. The areal implant of claim 1, wherein the weight of the flexible knitted fabric is less than 50 g/m².

5. The areal implant of claim 1 wherein the flexible knitted fabric has a structure selected from the group consisting of a honeycomb structure, an approximate rectangular structure and approximate quadratic structure knitted from yarns.

6. The areal implant of claim 1 wherein the flexible knitted fabric has a rectangular structure.

7. The areal implant of claim 1 wherein the flexible knitted fabric has an aproximate quadrate structure knitted from yarn.

8. The areal implant of claim 1 wherein the synthetic resorbable material is knitted into the flexible knitted fabric.

9. The areal implant of claim 8, wherein the flexible knitted fabric has a film flexible knitted fabric which is applied to one side thereof.

10. The areal implant of claim 8, wherein a coating is applied to the flexible knitted fabric.

11. The areal implant of claim 10, wherein the coating comprises polyglactin 630.

12. The areal implant of claim 10, wherein the synthetic resorbable material comprises a material which is selected from the group consisting of: polymers based on caprolactone, polyglycolide, polylactide, poly-p-dioxanone, lactide/glycolide copolymers, lactide/caprolactone copolymers, glycolide/caprolactone copolymers, glycolide/poly-p-dioxanone copolymers, glycolide/poly-p-dioxanone/lactide copolymers, and other copolymers of the listed material.

13. The areal implant of claim 8, wherein the flexible knitted fabric is made of a material selected from the group consisting of polypropylene, polyester, and combinations thereof.

14. The areal implant of claim 8, wherein the synthetic resorbable material comprises a material which is selected from the group of the following materials: polylactide, polyglycolide, lactide/glycolide copolymers, polyglactin 910, and poly-p-dioxanone.

15. The areal implant of claim 8, wherein the flexible knitted fabric is not dyed.

16. The areal implant of claim 8, wherein the synthetic resorbable material is dyed.

* * * * *